United States Patent
Gauthier

[11] 3,965,890
[45] June 29, 1976

[54] SURGICAL RETRACTOR

[76] Inventor: William Kohlmann Gauthier, 310 Codifer Blvd., Metairie, La. 70005

[22] Filed: Oct. 18, 1974

[21] Appl. No.: 515,857

[52] U.S. Cl. ................................. 128/20; 403/79
[51] Int. Cl.² ..................... A61B 17/02; A61B 1/32
[58] Field of Search ............ 128/20, 17, 348, 350, 128/303; 287/14, 51 R

[56] References Cited
UNITED STATES PATENTS

| | | | |
|---|---|---|---|
| 1,816,642 | 7/1931 | Fettor | 40/330 |
| 3,068,728 | 12/1962 | Shepherd | 403/79 X |
| 3,509,873 | 5/1970 | Karlin et al. | 128/17 |
| 3,572,326 | 3/1971 | Jensen | 128/20 |
| 3,724,449 | 4/1973 | Gauthier | 128/20 |
| 3,749,088 | 7/1973 | Gauthier | 128/20 |

FOREIGN PATENTS OR APPLICATIONS

| | | | |
|---|---|---|---|
| 686,445 | 1/1953 | United Kingdom | 128/348 |

*Primary Examiner*—Lawrence Charles
*Attorney, Agent, or Firm*—Shoemaker & Mattare, Ltd.

[57] ABSTRACT

A surgical retractor comprises a frame on which a plurality of retractor arm mounting members are mounted for movement along the frame, and retractor arms are carried by the mounting members for movement of the arms transversely of the frame, and collapsible and extensible retractor blades are carried by the arms. The retractor blades include a plurality of blade sections having interengagable stops thereon to limit extension of the sections, and the stops are selectively movable to inoperative position to enable disassembly of the blade sections. The blades also are provided with flexible guards to prevent damage to flesh engaged by the blades and a finger tab to facilitate collapse and extension of the blades. Further, a "tailpiece" blade is carried by a retractor arm at an end portion of the frame, and the tailpiece blade is of one-piece construction and is configured to effectively engage flesh at the edge of an incision in a manner to prevent the lower edge of the blade from gouging the flesh and also to prevent the blade from "riding up" out of the incision. Moreover, a retractor blade mounting arm is provided which includes a pivotal section to facilitate mounting of a blade to the frame after other blades are in position, and also to permit an outer end portion of the arm to be pivoted out of the way of a surgeon.

11 Claims, 22 Drawing Figures

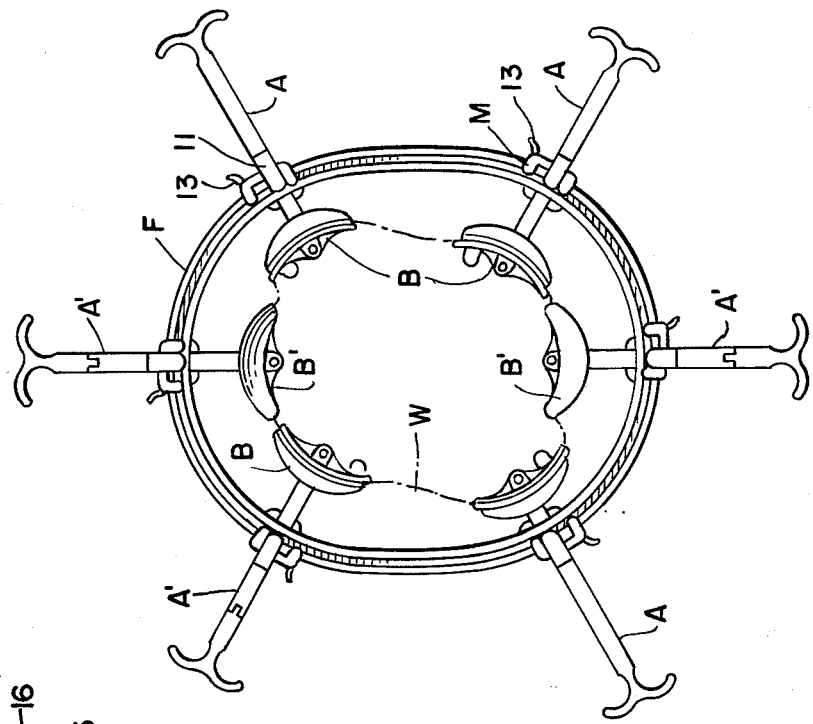
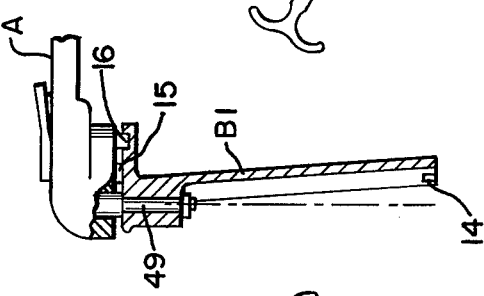
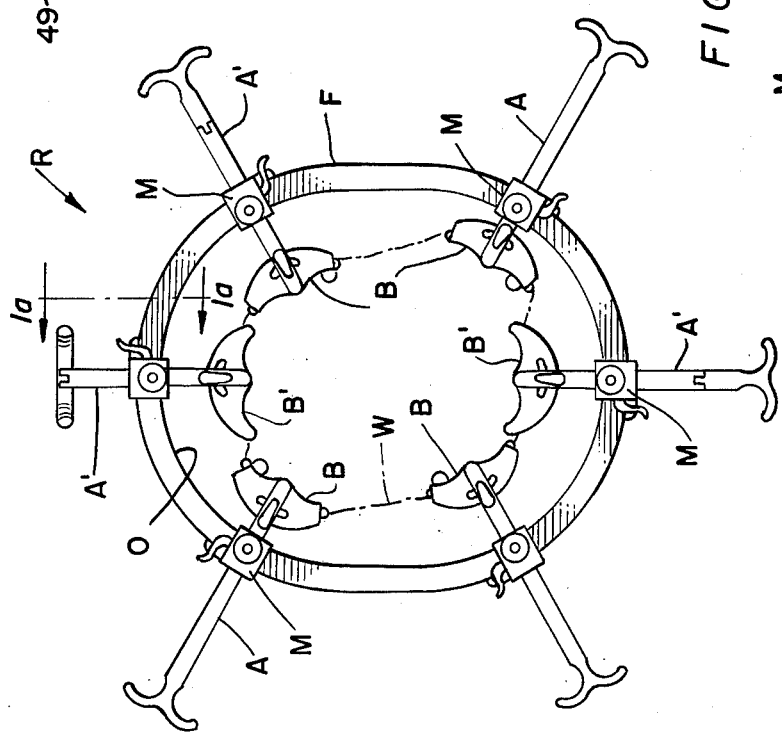
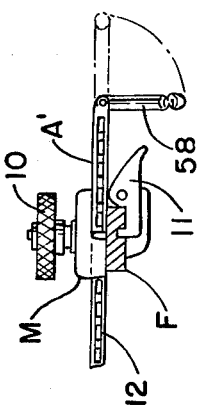

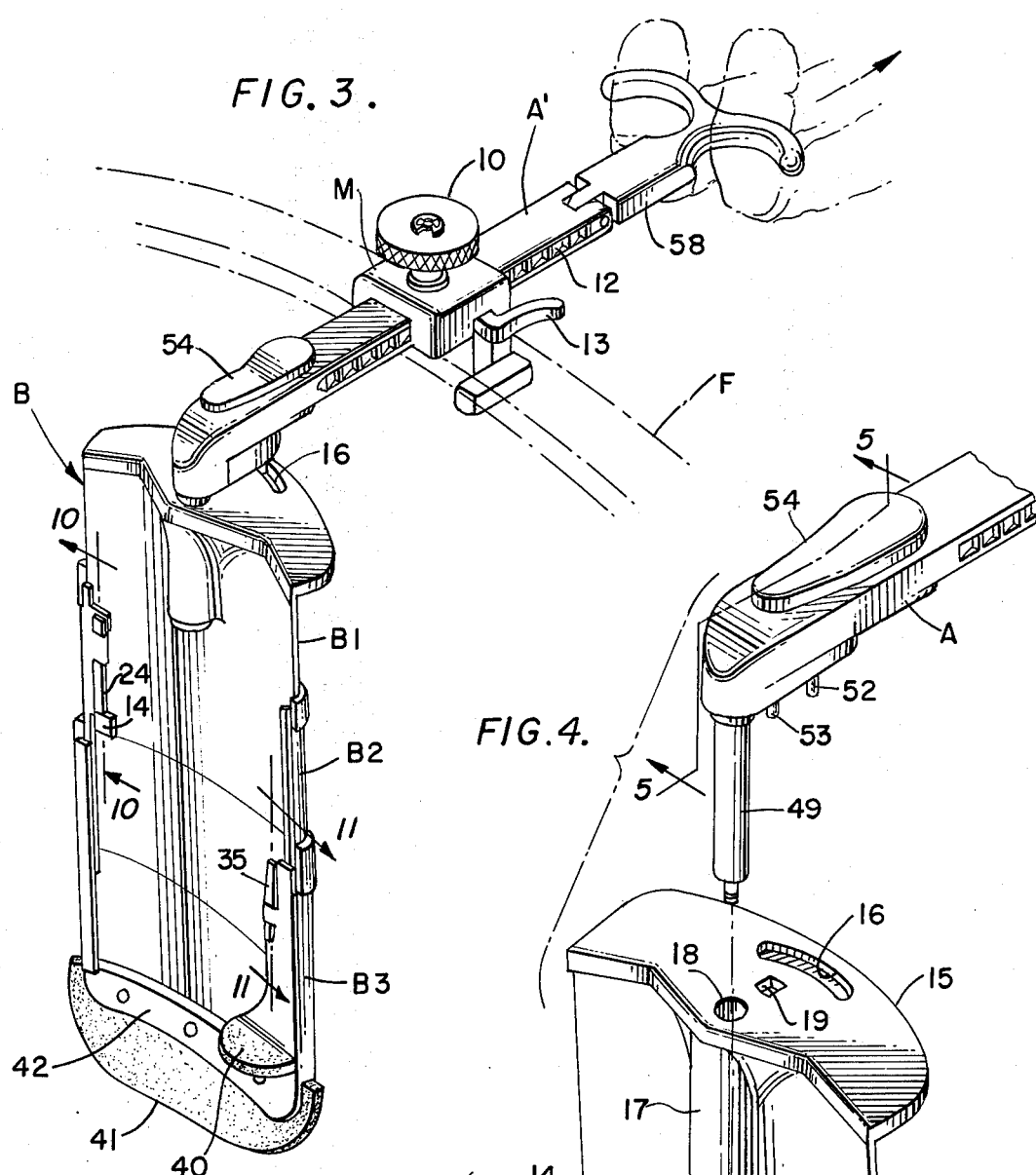
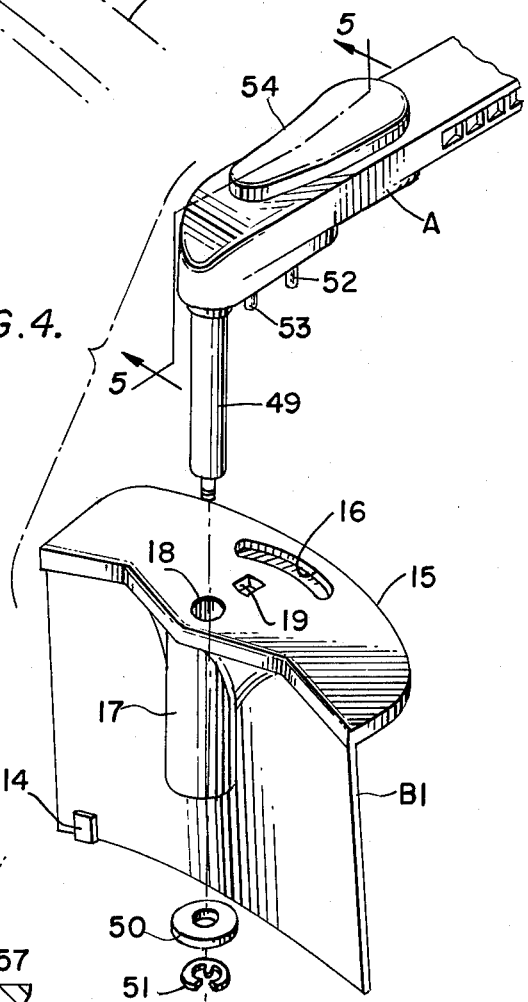
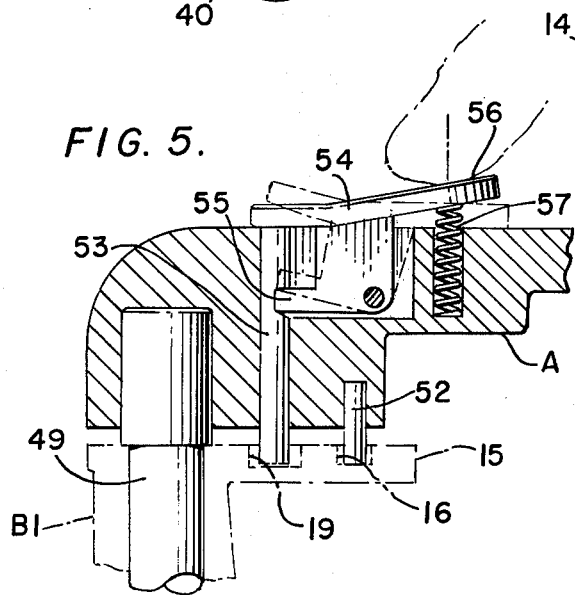
FIG. 3.
FIG. 4.
FIG. 5.

SURGICAL RETRACTOR

BACKGROUND OF THE INVENTION

This invention relates generally to surgical retractors, and more particularly to a surgical retractor which includes a frame having a plurality of retractor arms carried thereby and with retractor blades carried by the arms and depending therefrom for placement in an incised wound to engage the flesh at the edges of the wound to pull the flesh out of the way of a surgeon during the performance of an operation.

Many different types of surgical retractors as broadly outlined above are known in the prior art, and the present invention is directed to various improvements in surgical retractors. The surgical retractor according to the present invention possesses several unique advantages over prior art devices.

For example, the retractor blade of the present invention includes a plurality of telescopically interengaged blade sections, whereby the length of the blade may be extended or collapsed to accommodate itself to various depths of incisions, and interengaging stop means are on the blade sections to limit extension of the blade sections and to maintain the blade sections in assembled relationship. In the prior art, complete disassembly of the blade from the arm is generally necessary in order to disassemble the blade sections for cleaning and sterilization thereof. With the present invention, the stop means are selectively movable to an inoperative position to enable the blade sections to be slid or extended out of engagement with one another and thus disassembled for cleaning or sterilization, and without requiring removal of the blade from the arm. Further, the blade of the present invention is mounted to the arm for pivotal movement through a predetermined angular displacement, whereby the blade seeks its own position relative to the flesh at the edge of an incision, and one or the other of the edges of the blade will thus not dig into or gouge the flesh. The means for thus mounting the blade is exceptionally simple and rugged, and comprises a single movable stop pin engagable with an opening to lock the blade in a centered position, and an arcuate slot having a pin engaged therein, whereby positive limits of angular movement of the blade are defined when the movable pin is released from its opening.

Still further, the relatively movable blade sections in the telescoping blade have flexible guard means thereon which prevents pinching of flesh between adjacent blade sections during use of the blade.

Additionally, a finger tab is provided on a lowermost blade section of a plurality of telescopically interengaged blade sections to facilitate collapse and extension of the blade sections.

Further, in accordance with the present invention a unique means of attaching a flexible tip to a retractor blade is disclosed, whereby existing retractor blades as well as future retractor blades can be provided with a flexible tip to prevent tissue necrosis and the like. In other words, not only can retractor blades be manufactured with the flexible tip thereon, but retractor blades already in use can have the flexible tips applied thereto, and thus obtain the benefits of the flexible tip without requiring purchase of an entire blade.

Still further, in accordance with the present invention a retractor arm having a pivotal section therein is provided to facilitate application and removal of an arm and its associated blade to the frame and placement of the blade in an incised wound after other blades are already positioned. Additionally, the pivot means enables the outer end portion of the arm to be pivoted out of the way of a surgeon during the performance of an operation.

Another unique part of the present invention is a novel tailpiece blade which comprises an improvement over the conventional Balfour blade, and the tailpiece blade of the present invention is of one-piece construction and has a compound curvature such that it extends below and gathers the fatty flesh at the edge of an incision to hold the fatty flesh upwardly and outwardly out of the way of a surgeon. The configuration of the tailpiece blade is such that the lower edge thereof does not gouge into the flesh, as do prior art blades of this type. Further, the tailpiece blade (as well as the collapsible blades heretofore described) has its pivot axis disposed at right angle relative to the axis of the arm, and the blade itself is inclined rearwardly relative to the pivot axis, whereby the blade extends slightly rearwardly to prevent the blade from riding up out of an incision when in use.

OBJECTS OF THE INVENTION

It is an object of this invention to provide a retractor blade comprising a plurality of telescopically interengaged sections having stop means thereon which is movable to an inoperative position to enable the blade sections to be disassembled for cleaning and the like.

Another object of this invention is to provide a retractor blade means wherein the retractor arm has a pivotal section therein to facilitate application and removal of the arm and associated blade to and from a frame, and also to enable the outer end portion of the arm to be pivoted out of the way of a surgeon.

A still further object of the invention is to provide a flexible tip for application to existing blades, as well as to blades manufactured hereafter, to prevent tissue necrosis to flesh engaged by the blade.

Yet another object of the invention is to provide a unique tailpiece blade which is of one-piece construction and has a compound curvature and configuration such as to engage the flesh at the edge of an incision and gather the flesh upwardly and outwardly to hold the flesh out of the way of a surgeon performing an operation, and without gouging the flesh with the lower edge portion of the blade.

A still further object is to provide a unique retractor blade construction, wherein the blade is pivotally mounted to an arm and the means mounting the blade to the arm includes an arcuate slot and a stop pin engaged in the slot to limit the angular displacement of the blade relative to the arm.

A further object of the invention is to provide a collapsible and extensible retractor blade comprising a plurality of telescopically interengaged sections, wherein a finger tab is on a lowermost section to facilitate extension and collapse of the section.

Another object of the invention is to provide a retractor blade means comprising a plurality of telescopically interengaged blade sections which are extensible and retractable to change the blade length to accommodate different depths of incision, and wherein flexible guard means is attached to the upper edge of a lower blade section for sliding movement with an adjacent surface of an upper blade section to prevent pinching of flesh and the like between the blade sections.

Other objects and advantages of the invention will appear from a study of the detailed description which follows.

BRIEF DESCRIPTION OF THE DRAWINGS

FIG. 1 is a top plan view of a retractor embodying the features of the present invention and shown is position relative to an incised wound.

FIG. 1a is a fragmentary view in section taken along line 1a—1a of FIG. 1.

FIG. 2 is a bottom plan view of the retractor of FIG. 1.

FIG. 3 is a greatly enlarged, fragmentary, perspective view of a portion of the apparatus of FIG. 1, and showing one of the retractor arms and blades in accordance with the invention.

FIG. 4 is an enlarged, fragmentary, perspective, exploded view of a portion of the arm and blade means of FIG. 3.

FIG. 5 is a greatly enlarged, sectional view taken along line 5—5 in FIG. 4.

FIG. 21 is a view in section similar to FIG. 20 of the telescopic blade means illustrating the angular disposition of the blade means relative to the pivot axis and arm.

DETAILED DESCRIPTION OF THE INVENTION

A surgical retractor R in FIG. 1 includes a closed, generally oval-shaped, one-piece frame F having a plurality of retractor arm mounting means or members M mounted thereto for movement therealong, a plurality of retractor arm means A and A' carried by the mounting members M for movement of the arms both along the frame and transversely of the frame. A plurality of retractor blades B and B' are carried by the arms A and A' and depend from the arms into the opening O defined by the frame F for engagement with the flesh about the edge of an incised wound W to hold the flesh out of the way of a surgeon performing an operation.

The frame F is of substantially conventional construction, as are the mounting members M and the retractor arms A, and these elements are fully described in applicant's U.S. Pat. No. 3,749,088, issued July 3, 1973. It is believed sufficient to point out here that the mounting members M are freely slidably movable along the frame F and are secured in adjusted position along the frame by tightening the knurled nut 10 carried by the mounting member, as described in the aforesaid patent. Further, the mounting members M carry pivotal latches 11 which have a flange engagable in the channel in the underside of the frame F, and ratchet means comprising a series of teeth 12 along one side of the arm A and a pawl 13 carried by the mounting member are provided, whereby the arm may be quickly and easily positioned in a desired location with the use of only one hand, thus freeing the surgeon for other duties during the performance of the operation.

Figure 10:
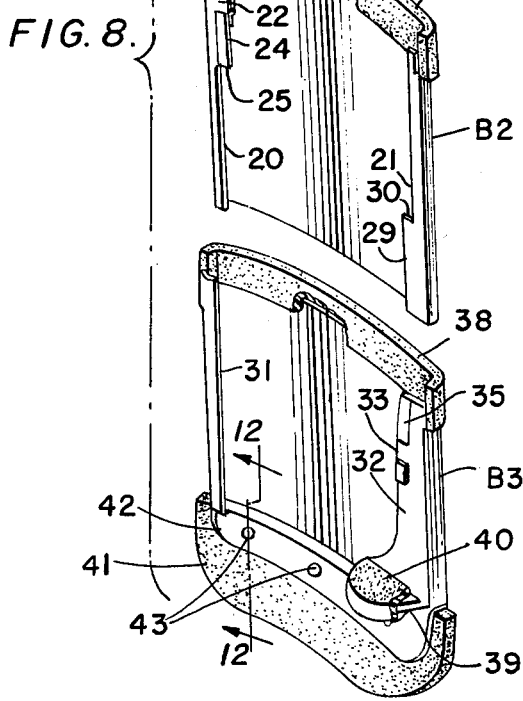
FIG. 10 is a greatly enlarged, sectional view of the blade shown in FIG. 8, and with the blades assembled and showing the manner in which the stop means engages an abutment to limit extension of the middle blade section relative to the upper blade section of FIG. 8.
Figure 11:
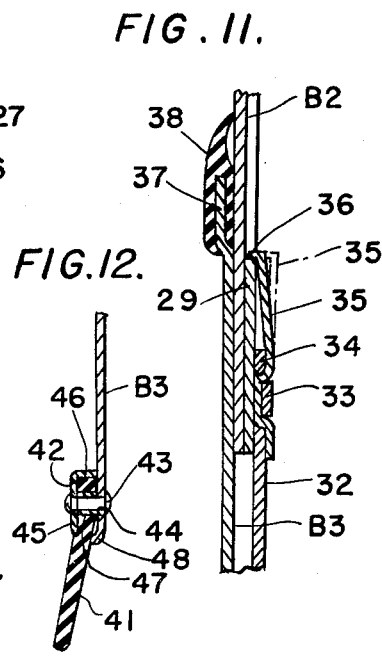
FIG. 11 is a view similar to FIG. 10, showing the stop means which is operative to limit extension of the bottom blade section relative to the middle blade section of FIG. 8.

As best seen in FIGS. 3–8, the blades B comprise a top blade section B1, a middle blade section B2 and a bottom blade section B3, all telescopically interengaged. The top blade section B1 has substantially plain opposite edge portions and is arcuately curved and includes a convex surface portion for engagement with the flesh at the edge of an incision to hold the incision open, and on the concave portion thereof adjacent a lower edge corner portion a stop abutment 14 is provided. Additionally, a rearwardly directed crescent or arcuately shaped lip 15 is integral with the upper edge portion of blade section B1 and has an arcuate slot or recess 16 formed in the upper surface near the arcuate edge thereof. A boss 17 extends downwardly along the concave face of the blade B1 from the lip 15 and an opening 18 extends axially therethrough. A third opening or recess 19 is in the upper surface of the lip 15 between opening 18 and arcuate slot 16. The middle blade section B2 has the opposite edges thereof turned inwardly at 20 and 21, defining channel structures thereat for sliding receipt of the opposite edges of the blade section B1. The inturned edge portion 20 includes a plurality of spaced apart, offset tabs 22 and 23, which grip and secure in position a movable stop 24 comprised of a material such as spring steel or the like and having a resiliently yieldable, elongate end portion 25, which engages against the upper edge surface of abutment 14 on blade B1 when the blades B1 and B2 are assembled together to limit the extension of blade section B2 relative to blade section B1, as seen in FIG. 10, for example. When it is desired to disassemble blade section B2 from blade section B1, the end portion 25 of stop member 24 is moved to the position shown in phantom line in FIG. 10, so as to clear the abutment 14 and permit the blade section B2 to move off of the end of blade section B1. Additionally, the upper edge of blade section B2 is offset laterally toward the convex face thereof, as at 26, and a flexible guard 27 is applied thereto and the guard is molded or bonded to the offset portion 26 and tapers to a thin upper edge 28, which partly due to the curvature of the blade sections, extends into sliding contact with the convex surface of blade B1 and thus prevents pinching of flesh between the blade sections B1 and B2 when in use. Further, the inturned edge portion 21 of blade section B2 is enlarged at 29, thus defining an upwardly facing shoulder 30 thereon. Blade section B3 similarly has the opposite edge portions thereof turned inwardly at 31 and 32, defining channel structures at opposite edges of the blade section which slidably receive the opposite edge portions of blade section B2. The inturned edge portion 32 of blade section B3 also has a plurality of spaced apart, offset tabs 33 and 34, which receive and securely grip a resiliently yieldable stop member 35, preferably made of spring steel or the like, and having an inturned end portion or lip 36 on an upper end thereof, which engages against the shoulder 30 on flange 21 of blade section B2 to prevent withdrawal of blade section B3 from blade section B2, and yet which is movable to the phantom line position indicated in FIG. 11 to enable the blade section B3 to be disassembled from blade section B2. Blade section B3 also has an offset upper edge portion 37, with a flexible guard 38 bonded thereto substantially identical to guard 27 on blade section B2. Further, the inturned edge portion 32 of blade section B3 is enlarged and bent perpendicularly to the plane of the blade at its bottom end 39 and is covered with a suitable resilient material, such as silicone or the like 40, and defines a finger tab to facilitate and extension and collapse of the blade sections during their use.

Figure 12:
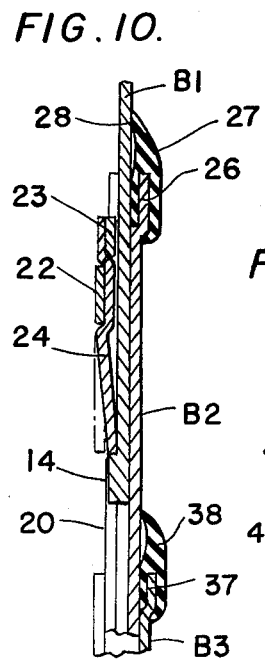
FIG. 12 is an enlarged, fragmentary view in section taken along line 12—12 in FIG. 8.

Additionally, in order to prevent tissue necrosis of flesh engaged by the blade, a flexible, resilient tip 41 is secured to the lower edge of bottom blade section B3 by means of a clamping plate 42, having an L-shaped cross-sectional configuration and a plurality of rivets 43 extended through openings 44 in the bottom edge of blade section B3 and through openings in the upper edge of tip 41 and through registered openings in a downturned wall portion 45 of plate 42. The plate 42 has an upper, rearwardly extending wall or flange 46, which extends into engagement with the concave surface of blade section B3, and a plurality of spacers made of aluminum or the like 47 are disposed through the openings in the upper end of tip 41 and between the concave surface of blade B3 and the depending wall 45 of plate 42 to prevent deformation of the tip 41 when the rivets are secured therethrough. When secured to the blade section B3, the tip 41 is caused to assume the curved configuration of the blade, and in fact, the tip 41 is deformed as illustrated in FIG. 12 to extend slightly rearwardly from the plane of the blade section B3, due primarily to the fact that the lower edge 48 of blade section B3 extends downwardly slightly beyond the lower edge of depending wall 45 of plate 42 and is slightly curled rearwardly toward the tip 41.

Figure 6:
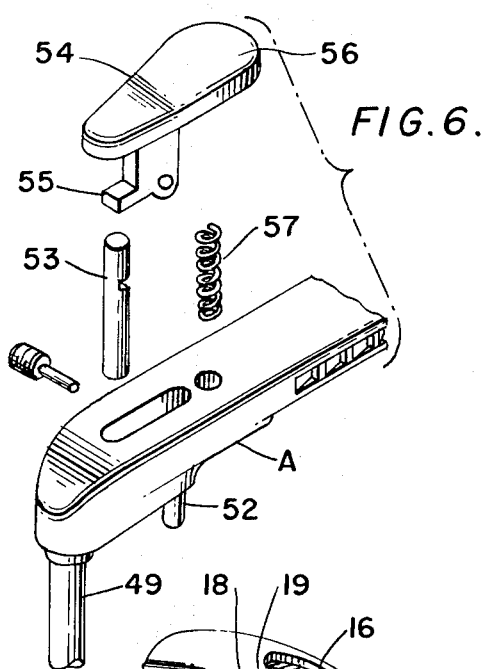
FIG. 6 is an enlarged fragmentary, perspective, exploded view of an end portion of one of the retractor arms showing the mechanism for operating the movable pin which locks the blade in a center position.
Figure 7:
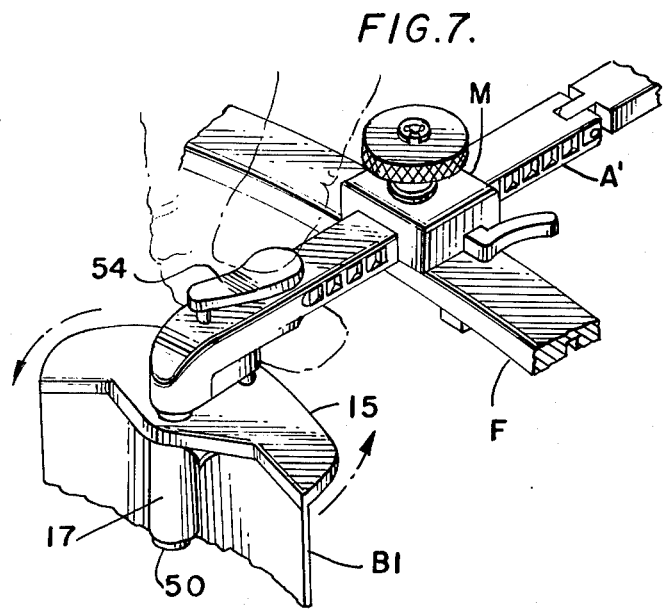
FIG. 7 is an enlarged, perspective, fragmentary view of a portion of the frame, retractor arm mounting means, retractor arm and blade according to the invention, depicting the manner in which the device of FIG. 6 is operated to enable pivotal movement of the blade.
Figure 8:
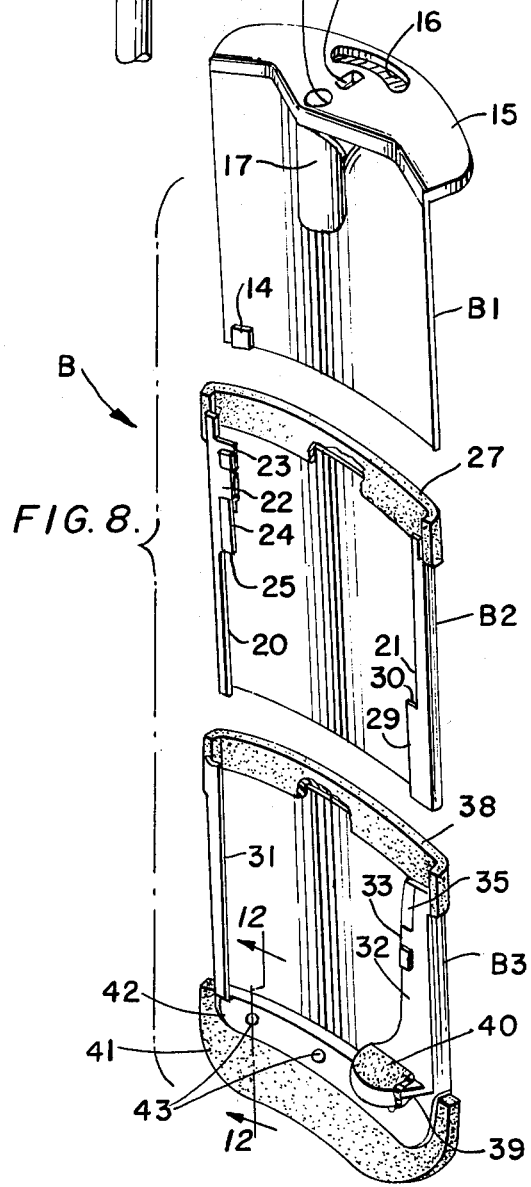
FIG. 8 is an enlarged, perspective, exploded view of a collapsible blade in accordance with the invention.

Pivotal movement of the blade relative to the arm A is effected by the structure of FIGS. 4, 5 and 6, and as seen in these FIGS., a fixed first pin 49 extends downwardly from the outer end of arm A and is pivotally received in the opening 18 of boss 17 on upper blade section B1. A washer 50 and snap ring 51 are secured to the lower end of pin 49 at the bottom end of the boss 17 for securely pivotally attaching the blade section B1 to the arm A. As thus secured, a second fixed pin 52 depending from the arm A in spaced relationship to fixed pin 49 extends into and is in registry with slot 16 and thus defines the limits of angular displacement of the blade section B1. A third, movable pin 53 is carried by the arm A between pins 49 and 52 in a position adapted to be placed in registry with opening 19 between opening 18 and slot 16 of blade section B1, whereby the blade may be locked in a center position, as illustrated in FIG. 3, for example. A lever 54 is pivotally connected to the arm A on the upper surface thereof, and has a forwardly projecting, pin engaging flange 55 which is operative to lift the pin 53 from opening 19 when a handle portion 56 of lever 54 is depressed against the influence of a coil spring 57.

Figure 9:
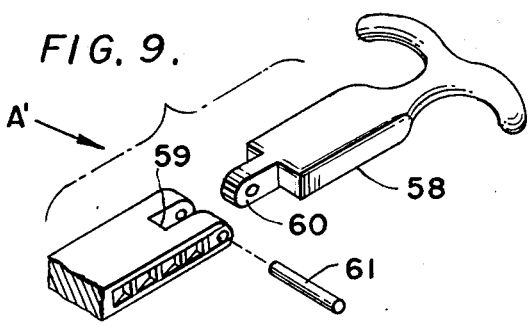
FIG. 9 is an enlarged, fragmentary, perspective, exploded view of a portion of a retractor arm showing the pivotal connection therein of the present invention.

The distal ends 58 of the arms A' are pivotally connected to the main body of the arms A', as illustrated in FIGS. 3 and 9, in order to facilitate application of the arms A' and associated blade to the frame F, and so that the distal ends 58 of the arms A' can be pivoted downwardly, thus in effect shortening the length of the arms A' and precluding interference of the ends of the arms with a surgeon or the like during the performance of an operation. The arms A' have a bifurcated end portion defining a slot 59 therein, and the distal end portions 58 of the arms have a forwardly or axially projecting boss or protrusion 60 thereon, which is received in the slot 59 and a pivot pin 61 extends through aligned openings in the bifurcated end portion and in the projection 60 to pivotally secure the distal end portion 58 to the arm A'.

Figure 14:
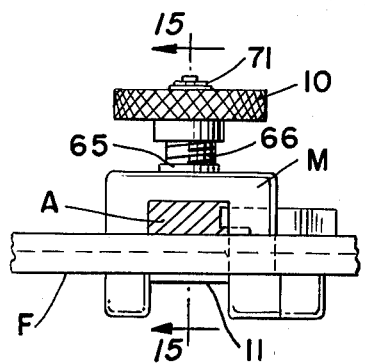
FIG. 14 is an enlarged, fragmentary view partly in section of the retractor arm mounting means.
Figure 15:
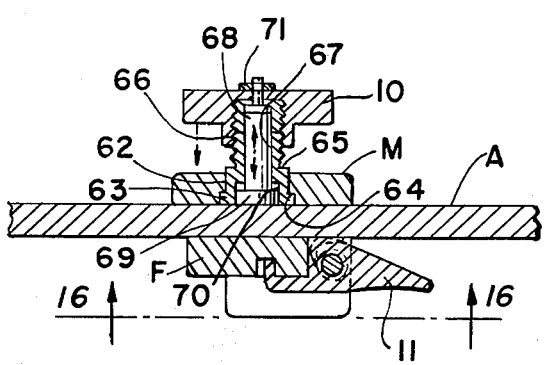
FIG. 15 is a view in section taken along line 15—15 of FIG. 14.

As seen in FIGS. 14 and 15, the clamp nut 10 for clamping the mounting member M in a predetermined, adjusted position along the frame F is threadably engaged on a unique sleeve member 62, preferably of stainless steel or the like, which has an enlarged flange 63 on its lower end received in a complementary recess 64 in the underside of the mounting member M and an upwardly facing shoulder 65 is formed on the outer surface of the sleeve 62, with a reduced diameter, externally threaded portion 66 extending upwardly therefrom. By this structure the sleeve 62 is positioned in the bore through the mounting member M, and a suitable tool is applied to the shoulder 65 and pressure is exerted thereagainst to swell or enlarge the sleeve 62 and swage it into secure engagement with the bore through the mounting member M. The sleeve 62 has a bore 67 extending axially therethrough, and a reciprocable pin 68 extends through the bore and has an enlarged head portion 69 on the lower end thereof slidably received in an enlarged diameter bore portion 70 in the lower end of the sleeve 62 and an upper end portion secured to the nut 10 by means of a snap ring 71 or the like, whereby as the nut 10 is threaded downwardly on the sleeve 62, it engages the upper end of pin 68 and forces the lower headed end 69 thereof downwardly against the upper surface of arm A to securely clamp the mounting member and arm in an adjusted position relative to the frame F, and when the nut 10 is threaded upwardly relative to sleeve 62, the pin 68 is pulled upwardly, releasing the clamping pressure. The snap ring 71 and length of pin 68 enable the nut 10 to be threaded completely off the threads on sleeve 62, but yet prevents complete separation or withdrawal of the nut 10 and pin 68 from the sleeve 62.

Figure 13:
FIG. 13 is a view similar to FIG. 12 of a modified means of attaching the flexible tip to the bottom blade section.
Figure 16:
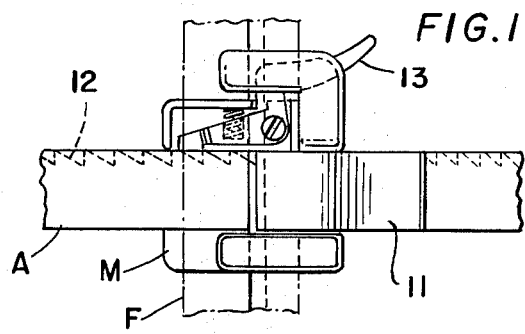
FIG. 16 is a bottom plan view taken along line 16—16 in FIG. 15.
Figure 17:
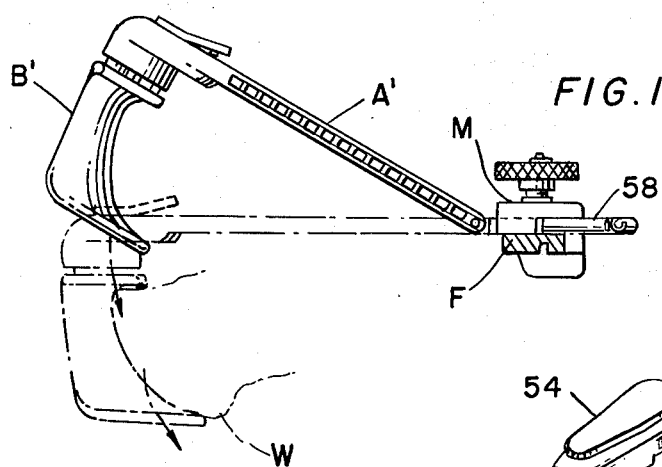
FIG. 17 is a view in elevation of a pivotal retractor arm having a tailpiece blade connected thereto, with the arm and blade shown in an elevated position in full lines and shown in operative position relative to an incised wound in phantom lines.
Figure 18:
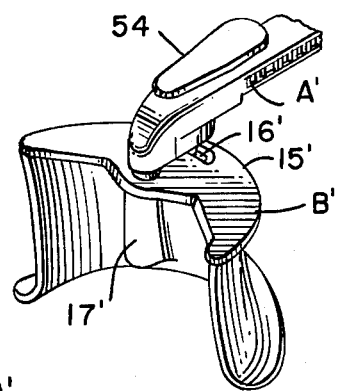
FIG. 18 is a fragmentary, perspective view of the tailpiece blade and a portion of the retractor arm of FIG. 17.
Figure 19:
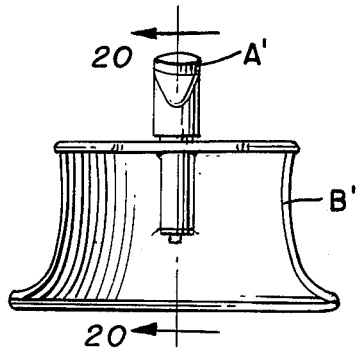
FIG. 19 is a front view in elevation of the blade of FIG. 18.
Figure 20:
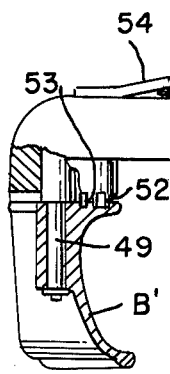
FIG. 20 is a view in section taken along line 20—20 of FIG. 19.

A modified flexible tip 41' is illustrated in FIG. 13, and in this form of the invention the tip is cast or bonded to the lower edge of blade section 53 and includes a portion of material on both the convex and concave face of blade section B3, and the material of the flexible tip 41' extends through aligned openings 44 in the blade section B3 to effect a secure connection of tip 41' to blade section B3.

The tailpiece blade B' is illustrated in FIGS. 17–20, and this blade is intended to replace the one-piece, Balfour blade currently in use. The manner of attachment of blade B' to arm A' is identical to that previously described and utilizes first and second fixed pins 49 and 52, and a movable pin 53. As distinguished from conventional Balfour blades, the tailpiece blade B' has a curvature such that when it is in position it curves beneath the flesh at the edge of a wound W and effects an uplifting force on the flesh and there is no gouging of the flesh by the lower edge of the blade. Moreover, the blade B', as well as the blades B previously described, are rearwardly inclined relative to their pivot axis (see FIGS. 8, 17, 20 and 21), such that the tendency of the blades to ride up out of the incision is reduced.

Further, in all of the collapsible blades described herein the guard material applied to the blade sections is preferably made of silicone and is color coded such that for blades having different extended and collapsed lengths different colors are used, whereby in the urgency of an operating room atmosphere a nurse or other attendent may quickly identify and properly select blade sections or blades of the proper length to be used. Moreover, the silicone material is impregnated with barium sulfate whereby any parts of the material which may become lost in an incision may be readily discovered by X-ray procedures.

Additionally, the frame, arms and blades are preferably made of wrought aluminum, which may be anodized or chrome plated or otherwise suitably treated.

Thus, the retractor apparatus is light in weight and yet is strong and durable, and the potentially harmful elements of the apparatus are rendered safe by means of the flexible guards and unique construction of the apparatus.

Further, the unique collapsible features, pivotal adjustments, ratchet mechanisms and pivoted arms make the retractor exceptionally easy to use, and a person may readily position and adjust the apparatus with the use of only one hand and without requiring manipulation of separate fasteners or parts to secure the retractor components in their proper operative positions.

As this invention may be embodied in several forms without departing from the spirit or essential characteristics thereof, the present embodiment is, therefore, illustrative and not restrictive, since the scope of the invention is defined by the appended claims rather than by the description preceding them, and all changes that fall within the metes and bounds of the claims or that form their functional as well as conjointly cooperative equivalents are, therefore, intended to be embraced by those claims.

I claim:

1. A surgical retractor comprising a frame means, retractor arm means carried by the frame means, retractor blade means carried by the arm means at one end of the arm means and depending therefrom for placement in an incised wound to hold the flesh out of the way of a surgeon, and pivot means pivotally mounting the blade means to the arm means for pivotal movement of the blade means about an axis disposed perpendicular to the axis of the arm means, said pivot means including a first fixed pin depending from the end of the arm means and pivotally received in an opening in the blade means for pivotal movement of the blade means about said first pin, said blade means rearwardly angularly inclined relative to said pivot axis whereby the blade is prevented from riding up out of an incision, a second fixed pin depending from the arm means in spaced relationship to the first pin and engaged at its lower end in an arcuate slot in an upper end portion of the blade means, so as to limit pivotal movement of the blade means to a predetermined angular displacement, and a movable stop pin carried by the arm and depending therefrom, said stop pin registerable with a hole in an upper end portion of the blade means so as to extend into said hole to preclude pivotal movement of the blade means, and actuating means connected with said movable stop pin to selectively retract said stop pin from said hole to enable said blade means to pivot about the first pin.

2. A surgical retractor blade means for use in holding flesh out of the way of a surgeon during performance of an operation, said blade means comprising a plurality of arcuately curved, relatively movable blade sections telescopically interengaged with one another for extensible and collapsible movement in a substantially vertical direction for accommodation to different depths of wounds, said blade sections having interengaged channel means at opposite edge portions thereof mounting them together for said relative movement, stop means on the blade sections interengagable to limit said extensible movement and thus maintain the blade sections in assembled relationship, synthetic plastic guard means fixed on the upper edges of subadjacent blade sections and in sliding engagement with the adjacent flesh engaging surface of an upper blade section to prevent pinching of flesh between the blade sections, and the flexible, synthetic plastic tip is fixed on the lower edge of the lowermost blade section to prevent tissue necrosis of flesh engaged by the blade.

3. A surgical retractor blade means as in claim 2, wherein the tip and flexible guard means are impregnated with barium sulfate to thus render them radioactively opaque, and are color coded to indicate different lengths of blades and thus to enable quick and easy identification of the proper length of blade to be selected for use during an operation.

4. In a surgical retractor blade means for use in holding flesh out of the way of a surgeon during performance of an operation, wherein said blade means comprises a depending blade section having a free lower edge portion, the improvement comprising a flexible, synthetic plastic tip secured to the lower edge of the blade section, said flexible tip including an upper edge portion overlapped with the lower edge portion of the blade section and bonded thereto in flush, abutting contact therewith, the lower edge portion of the blade section having openings therethrough and separate tip fastening means extended through aligned openings in the upper edge portion of the tip and said openings in the blade section to secure the tip to the blade section.

5. A surgical retractor blade means as in claim 4, wherein said separate fastening means comprises rivets and a blade tip clamping member is engaged against the upper edge portion of the tip and comprises a flange extending across the upper edge of the tip and into engagement with an adjacent portion of the blade section, and a depending wall portion extending downwardly over a portion of the tip and clamping the tip between the lower edge portion of the blade section and the clamping member, said rivets extended through the blade sections, the tip and the clamping member.

6. A surgical retractor blade means as in claim 5, wherein sleeve means are positioned in openings through the tip, between the clamping member and blade section to prevent crushing and deformation of the tip when the rivets are secured therethrough.

7. A surgical retractor blade means as in claim 6, wherein a bonding agent is disposed between the tip and the adjacent portion of the blade section.

8. A surgical retractor blade means as in claim 4, wherein the tip is molded in situ to the lower edge of the blade section and on both the concave and convex surfaces of the blade section, the lower edge of the blade section having a plurality of openings therethrough and the material of the tip extended through said openings.

9. In a surgical retractor including a frame means, retractor arm means carried by the frame means and retractor blade means carried by the arm means and depending therefrom for engagement with flesh in an incised wound to hold the flesh out of the way of a surgeon during the performance of an operation, the improvement comprising a pivotal section between the ends of the retractor arm means to facilitate application and removal of the retractor arm means and an associated blade means to and from the frame means, and to enable an outer end portion of the arm to be pivoted to shorten the length of the arm extending beyond the frame means to eliminate interference of the arm with the surgeon.

10. A surgical retractor as in claim 9, wherein the retractor blade means is of rigid, one-piece construction and has a compound curvature for engagement with the flesh adjacent an end of an incision, said blade mounted for pivotal movement about a pivot axis extended downwardly and slightly rearwardly relative to the axis of the retractor arm to which it is mounted.

11. In a surgical retractor blade means including a plurality of telescopically interengaged blade sections to enable the length of the blade sections to be adjusted, the improvement comprising selectively releasable stop means on the blade sections, said stop means including a movable stop carried by one blade section in a position for engagement with an abutment on an adjacent blade section to limit extension of the blade sections relative to one another, said movable stop selectively movable laterally relative to its associated blade section out of the path of the abutment to enable the blade sections to be separated from one another in the direction of blade extension.

* * * * *